United States Patent
Nyce

[19]

[11] Patent Number: 6,136,791
[45] Date of Patent: Oct. 24, 2000

[54] AGENT AND METHOD FOR TREATING DISORDERS ASSOCIATED WITH CYTIDINE DEAMINASE OR DEOXYCYTIDINE DEAMINASE OVEREXPRESSION

[75] Inventor: Jonathan W. Nyce, Greenville, N.C.

[73] Assignee: East Carolina University, Greenville, N.C.

[21] Appl. No.: 08/772,455

[22] Filed: Dec. 23, 1996

Related U.S. Application Data

[63] Continuation-in-part of application No. 08/577,185, Dec. 22, 1995, abandoned.

[51] Int. Cl.[7] ................................................. A01N 43/04
[52] U.S. Cl. ................................ 514/43; 514/49; 514/50; 514/885
[58] Field of Search ................................ 514/49, 50, 885, 514/43

[56] References Cited

U.S. PATENT DOCUMENTS

| | | | |
|---|---|---|---|
| 3,891,623 | 6/1975 | Vorbrüggen et al. | 260/211.5 R |
| 4,501,744 | 2/1985 | Ogilvie | 514/245 |
| 5,079,235 | 1/1992 | Purifoy et al. | 514/49 |
| 5,084,445 | 1/1992 | Chu et al. | 514/49 |
| 5,215,971 | 6/1993 | Datema et al. | 514/49 |
| 5,576,429 | 11/1996 | Johansson et al. | 536/26.8 |
| 5,652,099 | 7/1997 | Conrad | 536/27.7 |
| 5,728,525 | 3/1998 | Conrad | 536/24.3 |

OTHER PUBLICATIONS

T. Kulikowski et al.; Preparation and Properties of N[4]–Alkyl Analogues of 5–Methyl–2'–Deoxycytidine, Their 5'–Mono and Triphosphates, and N[4]–Alkyl Derivaties of 1,5–Dimethylcytosine, *ACTA Biochimica Polonica* 16:201–217 (1969).

J. J. Fox et al.; Thiation of Nucleosides. II. Synthesis of 5–Methyl–2'–deoxycytidine and Related Pyrimidine Nucleosides, 81:178–187 (1959).

T. Lin et al.; Synthesis and Biological Activity of Various 3'–Azido and 3'Amino Analogues of 5–Substituted Pyrimidine Deoxyribonucleosides, *J. Med. Chem.* 26, No. 12:1691–1696 (1983).

C. K. Chu et al.; Structure–Activity Relationships of Pyrimidine Nucleosides as Antiviral Agents for Human Immunodeficiency Virus Type 1 in Peripheral Blood Mononuclear Cells, *J. Med. Chem.* 32, No. 3:612–167 (1989).

C. Kim et al.; Potential Anti–AIDS Drugs. 2',3'–Dideoxycytidine Analogues, *J. Med. Chem* 30:862–866 (1987).

F.D. Boudinot et al.; Pharmacokinetics and Metabolism of 3'Azido–2',3'–Dideoxy–5'–Methyl Cytidine in Rhesus Monkeys, *Drug Metabolism and Disposition* 21(5):855–860 (1993).

*Primary Examiner*—James O. Wilson
*Attorney, Agent, or Firm*—Viviana Amzel; Arter & Hadden LLP

[57] ABSTRACT

An agent of the chemical formula $C_7N_3H_8O_2R^1R^2XX^1$, wherein X and $X^1$ are each independently C or N but not simultaneously, $R^1$ is lower alkyl, alkenyl or alkynyl, halogen or haloalkyl, and $R^2$ is H, $-N_3$, $-OH$, amino or halogen; or pharmaceutically acceptable salts thereof. A method of treating a disorder associated with the overexpression of cytidine deaminase or deoxycytidine deaminase comprises administering to a subject in need of the treatment a compound of the chemical formula

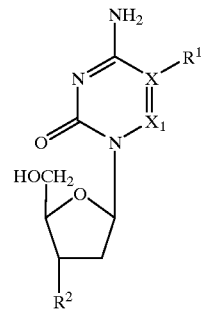

wherein
X and $X_1$ are each independently C or N; $R^1$ is lower alkyl, lower alkenyl, lower alkynyl, halogen, or haloalkyl; and $R^2$ H, $-N_3$, $-OH$, amino, or halogen; or a pharmaceutically acceptable salt thereof in an amount effective to treat the disorder. Pharmaceutical formulations useful in the method of the present invention are also disclosed.

87 Claims, 1 Drawing Sheet

AGENT AND METHOD FOR TREATING DISORDERS ASSOCIATED WITH CYTIDINE DEAMINASE OR DEOXYCYTIDINE DEAMINASE OVEREXPRESSION

This application is a continuation-in-part application of U.S. patent application Ser. No. 08/577,185, filed Dec. 22, 1995 now abandoned.

This invention was made with Government support under Grant No. CA47217, awarded by the National Cancer Institute. The Government has certain rights in the invention.

BACKGROUND OF THE INVENTION

1. Field of the Invention

The present invention relates to an active agent of the formula I and to a method of treating a disorder associated in part with the overexpression of cytidine deaminase or deoxycytidine deaminase, comprising administering 5-methyl-2',3'-dideoxy-3'-azidocytidine (5mAZC), analog thereof or a pharmaceutically effective salt thereof to a subject in need of such treatment in an amount effective to treat the disorder and ameliorate its symptoms.

2. Description of the Background

The overexpression of cytidine deaminase (CD) is associated with a number of human disorders. For example, certain kinds of leukemias are refractory to the widely used anti-cancer agent cytosine arabinoside (araC). The lack of response to araC has been found to be due primarily either to inactivation of the deoxycytidine kinase gene locus (whose product is required for activation of araC to its cancer-killing form), or to the overexpression of cytidine deaminase or deoxycytidine deaminase (which deactivates araC by deaminating it to an inactive form, araUracil). There is currently no adequate treatment to overcome this resistance to araC due to the cytidine deaminase or deoxycytidine deaminase overexpression.

The overexpression of cytidine deaminase is also implicated in the ineffective cycle of the human immunodeficiency virus (HIV), the virus implicated in AIDS. The initial states of HIV infection are characterized by overexpression of cytidine deaminase by the CD-4+T lymphocytes targeted by the virus. The elimination of this original set of infected cells could be critically important in controlling the level of subsequent infection.

Currently, one treatment for HIV infection and AIDS is the administration of 3'-azido-3'deoxythymidine (AZT). Problems with toxicity, however, have been associated with this treatment. Such toxicity occurs in part due to the fact that AZT is administered systemically, and damages host cells in all replicating tissue compartments.

There is currently a need for a treatment for HIV infection that has the same or improved efficacy of AZT, without the side effects associated with toxicity. One solution to this problem would be a prodrug for AZT which exhibited reduced toxicity to replicating cells, and was preferentially activated to its virus-killing form (AZT) in HIV-infected cells.

In addition, inflammatory cells associated with the symptoms of arthritis have also been shown to overexpress cytidine deaminase.

It would be desirable to provide a relatively non-toxic prodrug that would be preferentially activated to a metabolite that is toxic to the inflammatory cells mediating arthritis.

SUMMARY OF THE INVENTION

A method of treating a disorder associated with the overexpression of cytidine deaminase or by the overexpression of cytidine deaminase or deoxycytidine deaminase comprises administering 5-methyl-2',3'dideoxy-3'azidocytidine (5mAZC), an analog thereof or pharmaceutically acceptable salts thereof (hereinafter referred to as the "active compound"), to a subject in need of such treatment, in an amount effective to treat the disorder.

A method of treating a disorder associated with the overexpression of cytidine deaminase or deoxycytidine deaminase comprises administering to a subject in need of the treatment a compound of the chemical formula I

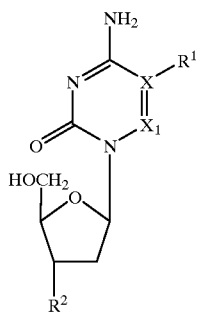

wherein
X and $X_1$ are each independently C or N;
$R^1$ is lower alkyl, lower alkenyl, lower alkynyl, halogen, or haloalkyl; and
$R^2$ is H, $-N_3$, $-OH$, amino, or halogen;
or a pharmaceutically acceptable salt thereof in an amount effective to treat the disorder.

A method of combatting leukemia resistant to cytosine arabinoside (araC) comprises administering a compound of chemical formula I to a subject in need of the treatment in an amount effective to combat araC-resistant leukemia.

A method of combatting HIV-infection in a subject comprises administering a compound of the chemical formula I to a subject in an amount effective to treat the HIV infection.

A method of combatting arthritis comprises administering a compound of the formula I to a subject in an anti-arthritis effective amount.

A method of combatting a cancer associated with the overexpression of cytidine deaminase or deoxycytidine deaminase, comprising administering to a subject in need of such treatment a compound of the chemical formula I in an anti-cancer effective amount.

A pharmaceutical composition comprises the active compound of this invention, and a pharmaceutically acceptable carrier (e.g., a sterile liquid or solid carrier).

The agent of this invention is suitable for the preparation of a medicament for carrying out the methods given above.

Figure 1:
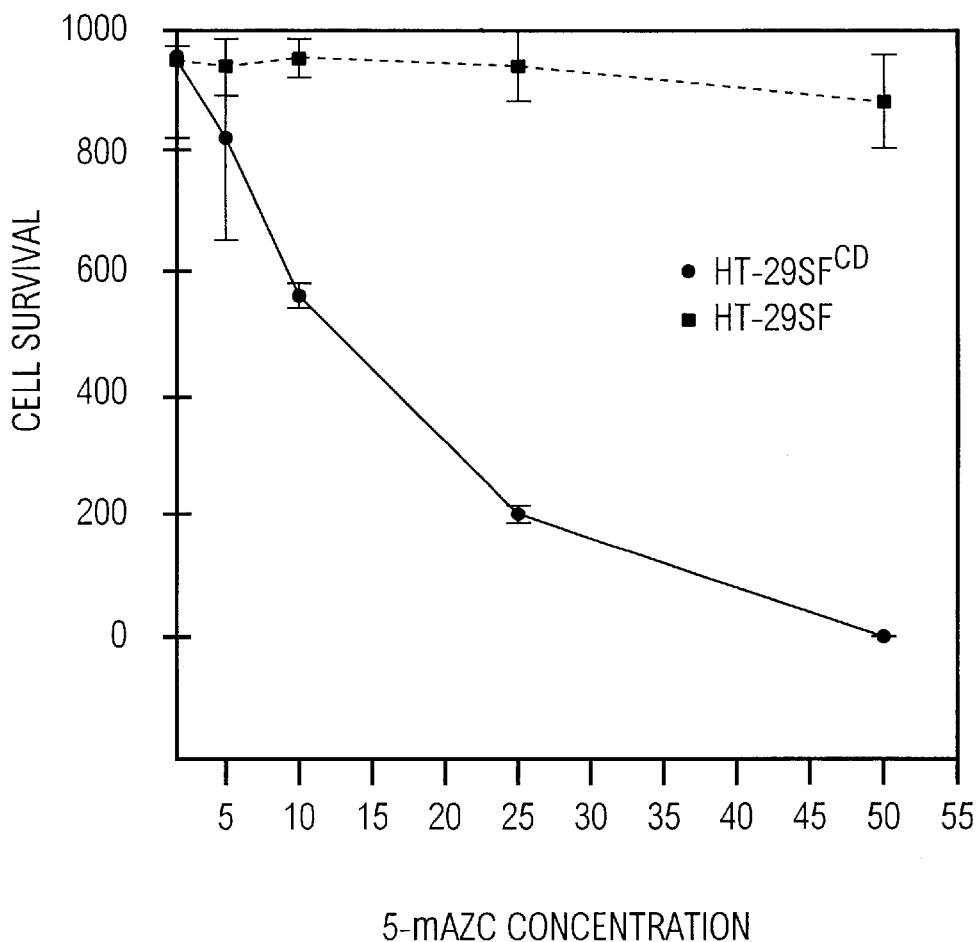
FIG. 1 is a graph of a dose response curve comparing the efficacy of 5mAZC in HT-29SF$^{CD}$ cells, which overexpress cytidine deaminase, and HT-29SF cells, which do not. HT-29SF cells were plated in the bottom compartment, and HT-29SF$^{CD}$ cells in the top compartment of a "Transwell" culture dish (1,000 cells each). A semipermeable membrane separate the two compartments of the Transwell, such that drugs administered in the tissue culture media bathed both compartments equally. The numbers of the x-axis indicate the concentration (in $\mu M$) at which 5mAZC was administered continuously for 72 hours; the numbers on the y-axis indicate the number of surviving cells. The circular (●) data points represent the dose response for the HT-29SF$^{CD}$ cells.

The square (■) data points represent the dose response for the HT-29SF cells.

DESCRIPTION OF THE PREFERRED EMBODIMENTS

The method of the present invention may be used to treat a subject suffering from a disorder associated with the overexpression of cytidine deaminase or deoxycytidine deaminase by administering 5-methyl-2',3'-dideoxy-3'-azidocytidine (5mAZC), an analog thereof, or pharmaceutically acceptable salts thereof (i.e. "active compounds") in an amount effective to treat the disorder. Examples of such disorders include, but are not limited to, cancer, leukemia that is resistant to cytosine arabinoside (araC), HIV infection, and arthritis. In a preferred embodiment, the method of the present invention is used to treat a subject suffering from a cancer that is characterized by the overexpression of cytidine deaminase. Examples of these cancers include adenocarcinoma of the colon, adenocarcinoma of the lung, adenocarciona of the stomach, adenocarcinoma of the breast, Wilm's tumor, chondrocarcinoma, chondrosarcoma, leukemia, prostate tumors, brain tumors (e.g., glioma, astrocytoma), kidney tumors, pancreatic tumors, cervical tumors, liver tumors (e.g., hepatoblastoma, hepatocarcinoma), neuroblastoma, retinoblastoma, melanoma, basal cell carcinoma, sarcoma, and cancers metastatic to the liver (e.g., colon cancer).

While applicants do not wish to be bound to any particular theory of the instant invention, it appears that 5mAZC is metabolized to 3'-azido-3'deoxythymidine (AZT) by cytidine deaminase and deoxycytidine deaminase, as illustrated in Scheme 1, below

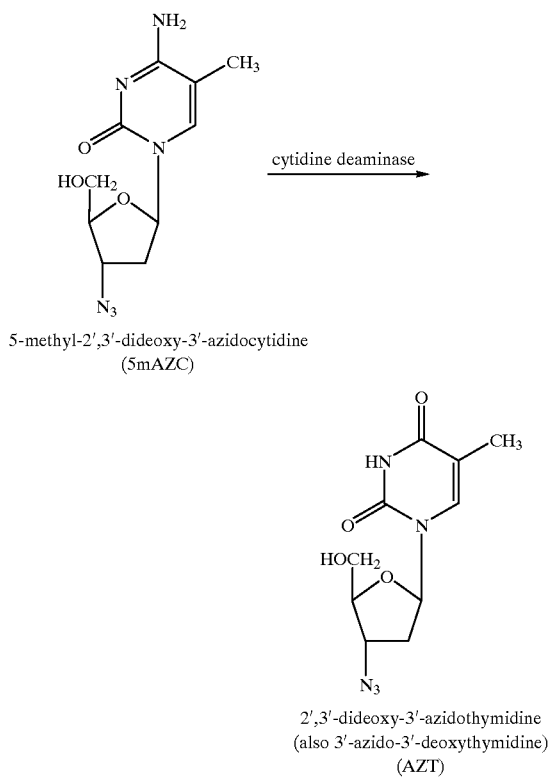

It appears that one effect of 5mAZC is facilitated by its preferential deamination to AZT in tumor cells that overexpress cytidine deaminase, while not adversely affecting cells that do not overexpress cytidine deaminase.

The present invention is concerned primarily with the treatment of human subjects but may also be employed for the treatment of other mammalian subjects, such as dogs and cats, for veterinary purposes.

As used herein, the term "lower alkyl," refers to C1 to C4 linear or branched alkyl, such as methyl, ethyl, propyl, butyl, isopropyl, sec-butyl, and tert-butyl. Methyl is currently preferred. As used herein the term "lower alkenyl," refers to C2 to C5 linear or branched alkenyl, such as ethenyl, propenyl, and butendyl. As sued herein, the term "lower alkynyl," refers to C2 to C5 linear or branched alykynl, such as propynyl and butynl. AS used herein, the term "haloalkyl" refers to a lower alkyl as defined above wherein one or more hydrogens is substituted with a halo-group (e.g., a chloro-, fluor-, bromo- or iodo-group), with —$CF_3$ being currently preferred.

Active compounds useful, in the practice of the present invention include compounds of to the chemical formula I

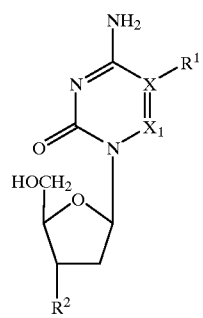

wherein

X and $X_1$ are each independently C or N;

$R^1$ is lower alkyl, lower alkenyl, lower alkynyl, halogen, or haloalkyl; and $R^2$ is H, —$N_3$, —OH, amino, or halogen.

In a preferred embodiment of the present invention, $R_1$ is methyl or —$CF_3$, and $R_2$ is —$N_3$ or —OH. In a particularly preferred embodiment of the invention, $R_1$ is methyl and $R_2$ is —$N_3$. Also encompassed herein are the pharmaceutically acceptable salts of these compounds.

Analogs of 5mAZC useful in the practice of the present invention include, but are not limited to, 5-methyl-2',3-dideoxycytidine, 5-ethyl-2',3'-5-propyl-2',3-dideoxycytidine, 5-propyl-2',3'-dideoxy-3'-azidocytidine, 5-propene-2',3'-dideoxycytidine, 5-propene-2',3'-dideoxy-3'-dideoxycytindine, and 5-propyne-2',3'dideoxy-3'-azidocytidine.

The structure of 5mAZC is known. See, e.g., T. S. Lin et al., *J. Med. Chem* 26, 1691–1696 (1983). 5mAZC is available from ChemSyn Laboratories (Lenexa, Kans., USA). Compounds useful for carrying out the present invention may be synthesized in accordance with known procedures which will be apparent to those skilled in the art. See, e.g. T. S. Lin et al., supra; T. Kulikowski et al., *Acta Biochim. Polonica* 16, 201–217 (1969); J. J. Fox et al., *J. Amer Chem. Soc.* 81, 178–187 (1959).

The active compounds disclosed herein may, as noted above, be prepared in the form of their pharmaceutically acceptable salts. "Pharmaceutically acceptable salts" are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalene sulfonic acid, methane sulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The dosage of the active compound utilized for treatment will vary depending on the condition and the state of the subject being treated. Generally, the dosage may be as low as 0.1 $\mu$mol/kg, but more preferably is at least 1.0 $\mu$mol/kg and most preferably is at least 25 $\mu$mol/kg. The dosage of the active compound may generally be as high as 1000 $\mu$mol/kg, but more preferably is less than 500 $\mu$mol/kg and most preferably is less than 100 $\mu$mol/kg. Depending on the solubility of the particular formulation of active compound administered, the daily dose may be divided among one or several unit dose administrations. Administration of the active compounds may be carried out therapeutically (i.e., as a rescue treatment) or prophylactically.

Pharmaceutical compositions for use in the present method of treating disorders associated with the overexpression of cytidine deaminase include those suitable for inhalation, oral, rectal, parenteral (including subcutaneous, intradermal, intramuscular, intravenous) and transdermal administration. The compositions may conveniently be presented in unit dosage form and may be prepared by any of the methods which are well known in the art. The most suitable route of administration in nay given case may depend upon the anatomic location of the disorder in the subject, the nature and severity of the condition being treated, and the particular formulation that is being used. The formulations may conveniently be presented in unit dosage form and may be prepared by any of the methods well known in the art.

In the present method of treating leukemia or other disorders associated with the overexpression of cytidine deaminase or deoxycytidine deaminase, the active compound is administered in a dose range as given above. The dose of active agent will vary according to the condition being treated and the dose at which adverse pharmacological effects occur. One skilled in the art will take such factors into account when determining dosage.

In one embodiment of the present invention, the active compound is administered to the subject with araC-resistant leukemia in an amount effective to be metabolized by cytidine deaminase or deoxycytidine deaminase to AZT in sufficient concentration to kill the araC-resistant cancer cells.

In a further aspect of the present invention, the active compound may be used alone or in combination with one or more anti-leukemia agents for the prophylaxis or treatment of araC-resistant leukemia.

In the manufacture of a pharmaceutical composition according to the invention (a "formulation"), active agents or the physiologically acceptable salts thereof (the "active compound") are typically admixed with, inter alia, an acceptable carrier. The carrier must, of course, be acceptable in the sense of being compatible with any other ingredients in the formulation and must not be deleterious to the subject. The carrier may be a solid or a liquid, or a mixture of both, and is preferably formulated with the compound as a unitdose formulation, fore example, a tablet, which may contain from 0.5% to 99% by weight of the active compound. One or more active compounds may be incorporated in the formulations of the invention, e.g., the formulation may contain one or more additional agents as noted above, which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes bringing into association the active compound and a suitable carrier, which may contain one or more accessory ingredients as noted above. In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding in a suitable machine, the powdered compound moistened with an inert liquid binder. Formulations for oral administration may optionally include enteric coatings known in the art to prevent degradation of the formulation in the stomach and provide release of the drug in the small intestine.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Liquid formulations of the present invention suitable for parenteral administration comprise sterile aqueous and nonaqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed capsules and vials, and may be stored in a freeze-dried (lyophilized) condition requiring only the addition of the sterile liquid carrier, for example, saline or water-for-injection immediately prior to use. Injection solutions and suspensions may be extemporaneously prepared from sterile powders, granules and tablets of the kind previously described.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

The following examples are provided to more fully illustrate the present invention and should not be construed as restrictive thereof. In the following examples, g means grams, h means hours, kg means kilogram, ml means milliliter, M means molar, µg means microgram, and µmol means micromoles, nmol means nanomoles, pmol means picomoles, µCi means microCuries.

EXAMPLES

Example 1

Effect of 5mAZC in Cells that Overexpress Cytidine Deaminase

HT-29SF human adenocarcinoma cells naturally express a high level of cytidine deaminase (CD). HT-29SF$^{CD}$ is a subline of the HT-29SF cell line that express even higher CD levels than normal (about 5.4 times the expression level of HT-29SF cells). In order to see whether cells that overexpress cytidine deaminase are more sensitive to 5mAZC than other cells, HT-29SF$^{CD}$ cells were plated in the top compartment of a Transwell culture dish, while HT-29SF cells were placed in the bottom compartment (1000 cells each). A semipermeable membrane separated the two compartments of the Transwell, such that drugs administered in the tissue culture media bathe both compartments equally. 5mAZC was administered continuously for 72 hrs. at concentrations ranging from 0 µM to 50 µM. The results of this experiment are shown in FIG. 1. The results of this experiment confirm the idea that cells that highly overexpress CD are sensitive to 5mAZC.

Example 2

In vitro Activity of 5mAZC

Based upon the results obtained in Example 1 above, a dose of 50 µM 5mAZC was selected for more in-depth analysis. Two experiments were performed, in quintuplicate, in the same Transwell dishes, containing the HT-29SF cells and the HT-29SF$^{CD}$ cells in compartments separated only by a membrane permeable to 5mAZC. The results are given below in Table 1.

TABLE 1

Exposure of HT-29SF & HF-29SF$^{CD}$ Human Colonic Adenocarcinoma Cells to 50 µM 5mAZC for 72 hrs. in Transwell Culture Dish.

| Experiment 1 Number of viable cells | | Example 2 Number of viable cells | |
|---|---|---|---|
| HT-29SF$^{CD}$ | HT-29SF | HT-29SF$^{CD}$ | HT-29SF |
| 33.8 ± 17.1 | 797 ± 68 | 45.4 ± 15.6 | 867.2 ± 29.4 |

Example 3

In vivo Activity of 5mAZC: Human Tumor Xenograft Model

To demonstrate that 5mAZC exhibits in vivo activity, two sixteen week old female Balb/C nu/nu mice were subcutaneously inoculated with 2.0×10$^6$ HT-29SF (non cytidine deaminase producing) cells in the left scapular region, and 2.0×10$^6$ HT-29SF$^{CD}$ (cytidine deaminase producing) cells in the right scapular region. One of these mice received twice daily intraperitoneal doses of 150 mg/kg of 5mAZC. The other mice received saline only. This treatment continued for 5 weeks, at which time the animals were euthanized and the solid tumors were dissected free and weighed. The examined tumors had the following weights.

1—HT-29SF$^{CD}$+5mAZC: 0.22 g±0.31 g (N=2)
2—HT-29SF+5mAZC: 1.02±0.13 g (N=2)
3—HT-29SF$^{CD}$+saline: 0.96 g (N=1)
4—HT-29SF+saline: 1.13 g (N=1)

In another experiment, thirty BALB/c nude mice received subcutaneous injections of 5×10$^6$ HT-29SF cells. Twelve of the animals received 600 mg/kg/day 5mAZC in the flank for 28 days. Eighteen animals received saline injections on the same schedule. On Day 29, the animals were sacrificed and the tumor volume was quantified by standard methods. The average tumor volume for the control group receiving saline was 509±292 mm$^3$. In contrast, the animals treated with 5mAZC had an average tumor volume of 273±97 mm$^3$, an average 46% reduction in size. These results show clearly that 5mAZC is activated in vitro and in vivo in molecular species exclusively toxic to tumor cells that overexpress cytidine deaminase.

Example 4

CD Overexpression in Colon Tumors: Ex vivo Patient Data

The hypothesis that cytidine deaminase (CD) is overexpressed in certain tumors as compared with normal tissue was demonstrated in experiments conducted with surgical specimens obtained from patient undergoing bowel resection for colon cancer. Specimens of tumor and adjacent normal tissue obtained from pathological evaluation ere assayed for CD activity using [$^3$H]-cytidine as a substrate, according to the method of R. L. Momparler and J. Laliberte, *J. Leukemia Res.*, 14(9), 751–54 (1990). Briefly, colon tumors and adjacent mucosa from surgical specimens were homogenized in 5mM Tris-Cl, pH 7.4, sonicated on ice in three 5-second pulses, and then adjusted to 50 mM Tris-HCl, pH 7.4. The homogenates were centrifuged at 12,000×g for 15 minutes at 4° C., and the homogenates stored at −70° C. until analysis. Protein concentration was determined using a BioRad protein assay kit and bovine gamma globulin was used as a standard.

For determination of cytidine deaminase activity, the reaction mixture (100 µL) contained 25 mM Tris-Cl, pH 7.4, 0.5 µCi of [$^3$H]-cytidine and 0.02–0.05 mg of homogenate tissue. Reactions were carried out at 37° C. for 30 minutes, then stoped with 3 mL of cold 0.001 N HCl. The reaction mixture was placed on Whatman P-81 phosphocellulose discs that were washed with 3 mL of H$_2$O, 1 mL of 0.1 N HCl, and 3 mL of H2O twice before use. The mixture was allowed to flow gently by gravity for 1 hr and then assayed for radioactivity. The results were normalized for protein content and expressed as nmol/min/mg protein. The results of this experiment are presented below in Table 2.

TABLE 2

EZ Vivo Patient Data: Cytidine Deaminase
Activity in Tumor vs. Normal Adjacent Mucosa

| Patient | Activity in Normal Mucosa Adjacent to Tumor nmol/min/mg protein | Activity in Adenocarcinoma Tumor n/mol/min/mg protein | Percentage Tumor CD Activity of Normal | p value |
|---|---|---|---|---|
| 1 | 13.26 ± 0.67 | 17.36 ± 0.24 | 130.92 | <.01 |
| 2 | 12.00 ± 0.50 | 15.49 ± 0.33 | 129.08 | <.01 |
| 3 | 8.81 ± 0.79 | 29.20 ± 0.54 | 331.44 | <.01 |
| 4 | 10.82 ± 0.63 | 12.98 ± 0.58 | 110/06 | <.01 |
|   |   | 18.38 ± 0.54 | 169.87 |   |
| 5 | 7.78 ± 0.22 | 9.25 ± 0.48 | 118.89 | <.05 |
| 6 | 17.32 ± 0.93 | 22.35 ± 0.39 | 129.04 | <.01 |
| 7 | 6.37 ± 0.89 | 18.69 ± 1.27 | 294.98 | <.01 |
| 8 | 9.63 ± 0.77 | 14.55 ± 1.17 | 151.09 | <.05 |
| 9 | 14.01 ± 0.89 | 20.09 ± 0.20 | 143.40 | <.01 |
| 10 | 6.06 ± 0.83 | 18.51 ± 0.89 | 305.22 |   |
| Average | 10.61 ± 3.6 | 17.91 ± 5.2 | 184 |   |
| HT-29SF | 11.96 ± 0.16 |   |   |   |

Example 5

Preferential Deamination of 5mAZC to AZT in Colonic Tumors

The hypothesis that 5mAZC is preferentially deaminated to AZT in human colonic tumors versus in normal adjacent mucosa was demonstrated in the same ex vivo samples described above in Example 4. Using [$^3$H]-5mAZC as a substrate, the [$^3$H]-AZT product of the enzymatic reaction was isolated by HPLC and the radiolabeled product quantitated as described in J. W. Nyce et al., *Proc. Natl. Acad. Sci USA* 90, 2960–2964 (1993). Briefly, procedures described in Example 4 were repeated with the following exceptions: Each reaction mixture contained 0.26 μCi of [$^3$H]-5mAZC. The reactions were terminated with 50 μL of 2M perchloric acid and the mixture separated by HPLC using a 4.6×25 cm Beckman Ultrasphere ODS with a mobile phase of 12.5% acetonitrile in 40 mM sodium acetate pH 7.0. Unlabeled 5mAZC and AZT were used to authenticate the resulting peaks. The fractions corresponding to radiolabeled 5mAZC and AZT were collected and assayed for radioactivity by scintillation counting. The results were normalized for protein content and expressed as pmol/min/mg protein, and are provided below in Table 3.

To confirm that the AZT found in the colonic tumor tissue was being produced by cytidine deaminase activity (see Scheme 1, above), the cytidine deaminase inhibitor tetrahydrouridine (THU) was added to the reaction mixtures containing tumor tissue homogenate and radiolabeled 5mAZC; the amount of radiolabeled AZT produced was assayed as above, then compared to the amount of radiolabeled AZT produced in reaction mixtures not containing THU. The results of this experiment are also provided in Table 3.

The foregoing Examples are illustrative of the present invention, and are not to be construed as limiting thereof. The invention is defined by the following claims, with equivalents of the claims to be included therein.

TABLE 3

Ex vivo patient data: Preferential 5mAZC
deamination to AZT in tumor vs. Normal adjacent mucose

| Patient # | Radiolabeled AZT in Normal Adjacent Tissue pmol/min/mg protein | Radiolabeled AZT in Colon Tumor Tissue pmol/min/mg protein | Percentage AZT in Tumor Tissue of Normal | p value |
|---|---|---|---|---|
| 1 | 117.14 ± 7.61 | 134.51 ± 14.92 | 114.83 |   |
|   |   | After THU: |   |   |
|   |   | 30.56 ± 4.22 |   |   |
| 2 | 128.76 ± 2.17 | 153.34 ± 8.70 | 119.09 | <.05 |
|   |   | After THU: |   |   |
|   |   | 50.48 ± 7.30 |   |   |
| 3 | 40.42 ± 1.18 | 304.04 ± 17.63 | 752.17 | <.01 |
|   |   | After THU: |   |   |
|   |   | 0.31 ± 0.31 |   |   |
| 4 | 77.52 ± 8.83 | 80.01 ± 20.23 | 103.33 | polyp |
|   |   | After THU: |   |   |
|   |   | 6.47 ± 6.47 | 178.88 | <.01 |
|   |   | 138.58 ± 1.44 |   |   |
|   |   | After THU: |   |   |
|   |   | 34.83 ± 2.17 |   |   |
| 5 | 144.28 ± 20.39 | 225.21 ± 44.91 | 156.09 |   |
|   |   | After THU: |   |   |
|   |   | 90.90 ± 26.41 |   |   |
| 6 | 126.75 ± 9.75 | 235.07 ± 11.74 | 185.46 | <.01 |
|   |   | After THU: |   |   |
|   |   | 74.84 ± 6.51 |   |   |
| 7 | 70.58 ± 16.31 | 164.62 ± 20.63 | 233.23 | <.05 |
|   |   | After THU: |   |   |
|   |   | 26.81 ± 1.46 |   |   |
| 8 | 51.91 ± 14.01 | 88.59 ± 13.80 | 170.64 |   |
|   |   | After THU: |   |   |
|   |   | 61.31 ± 4.57 |   |   |
| 9 | 89.05 ± 13.05 | 132.10 ± 4.84 | 148.34 | <.05 |
|   |   | After THU: |   |   |
|   |   | 39.88 ± 24.18 |   |   |
| 10 | 64.28 ± 6.00 | 147.80 ± 10.95 | 229.93 | <.01 |
|   |   | After THU: |   |   |
|   |   | 80.34 ± 16.86 |   |   |
| Average | 91.1 ± 36.0 | 172.5 ± 63 | 229 |   |

That which is claimed is:

1. An agent having the chemical formula

$$C_7N_3H_8O_2R^1R^2XX^1,$$

wherein X and $X^1$ are each independently C or N but not simultaneously C; $R^1$ is selected from the group consisting of lower alkyl, alkenyl and alkynyl, halogen and haloalkyl; and $R^2$ is selected from the group consisting of H, —$N_3$, —OH, amino and halogen; or pharmaceutically acceptable salts thereof.

2. The agent of claim 1, wherein $R^1$ is methyl and $R^2$ is —$N_3$.

3. The agent of claim 1, which is selected from the group consisting of 5-methyl-2',3'-dideoxycytidine, 5-ethyl-2',3'dideoxy-3'-azidocytidine, 5-ethyl-2',3'-dideoxy-3'-deoxycytidine, 5-propyl-2',3'-dideoxycytidine, 5-propyl-2',3'-dideoxy-3'-azidocytidine, 5-propene-2',3'-dideoxy-3'-azidocytidine, 5-propene-2',3'-dideoxycytidine, 5-propyne-2',3'-dideoxycytidine and 5-propyne-2',3'-dideoxy-3'-azidocytidine.

4. The agent of claim 1, or pharmaceutically acceptable salts thereof, having the structural formula,

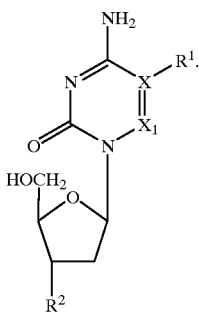

5. The agent of claim 4, wherein X comprises N and $X^1$ comprises C.

6. The agent of claim 4, wherein X comprises C and $X^1$ comprises N.

7. The agent of claim 4, wherein X comprises N and $X^1$ comprises N.

8. The agent of claim 1, further comprising a radiolabel.

9. The agent of claim 1, which is freeze-dried or lyophilized.

10. The agent of claim 1, wherein the $R^1$ haloalkyl is selected from the group consisting of alkyl substituted by one or more chloro, fluoro, bromo and iodo.

11. The agent of claim 10, wherein the $R^1$ fluoroalkyl comprises —$CF_3$.

12. A pharmaceutical composition, comprising an agent which is effective for countering cytidine aminase overexpression when administered to a mammal, the agent having the chemical formula $$C_7N_3H_8O_2R^1R^2XX^1,$$

wherein X and $X^1$ are each independently C or N; $R^1$ is selected from the group consisting of lower alkyl, alkenyl and alkynyl, halogen and haloalkyl; and $R^2$ is selected from the group consisting of H, —$N_3$, —OH, amino and halogen, or pharmaceutically acceptable salts thereof; and
a pharmaceutically acceptable carrier.

13. The composition of claim 12, comprising about 0.5 to about 99% of the agent.

14. The composition of claim 12, in unit dosage form.

15. The composition of claim 12, in multi-dosage form.

16. The composition of claim 12, in a form selected from the group consisting of capsules, cachets, pastilles, lozanges, powder, granules, solution, suspension, emulsion and tablets.

17. The composition of claim 12, wherein the carrier is selected from the group consisting of solid and liquid carriers.

18. The composition of claim 12, further comprising an agent selected from the group consisting of other therapeutic agents, flavorings, lubricants, suspending and thickening agents, binders, inert diluents, surface active agents, dispersants, antioxidants, buffers, bacteriostats and solutes to attain isotonicity.

19. The composition of claim 18, wherein the therapeutic agent comprises an anti-leukemia agent.

20. The composition of claim 19, wherein the anti-leukemia agent comprises cytosine arabinoside.

21. An oral formulation comprising the composition of claim 12, and an enteric coating.

22. A sub-lingual formulation comprising the composition of claim 12, wherein the flavoring and inert diluent are selected from the group consisting of sucrose, acacia, tragacanth, gelatin and glycerin.

23. A parenteral formulation comprising the composition of claim 12, comprising a solution, suspension or emulsion.

24. An ampoule or vial comprising the formulation of claim 12.

25. A rectal formulation comprising the composition of claim 12, in unit dosage form.

26. A transdermal formulation comprising the composition of claim 12, and an iontophoretic medium.

27. A transdermal device, comprising a patch which comprises the formulation of claim 26.

28. An iontophoretic device comprising the transdermal device of claim 27, and means for iontophoretic delivery.

29. A therapeutic kit, comprising in a sealed container the composition of claim 12, and instructions for its administration.

30. A method of treating a disorder associated with cytidine deaminase or deoxycytidine deaminase overexpression, comprising administering to a subject in need of treatment a composition comprising the agent of claim 1, in an anti-cytidine deaminase or cytidine deaminase overexpression effective amount.

31. The method of claim 30, wherein $R^1$ is methyl and $R^2$ is —$N_3$.

32. The method of claim 30, wherein the agent is selected from the group consisting of 5-methyl-2',3'-dideoxycytidine, 5-ethyl-2',3'dideoxy-3'-azidocytidine, 5-propyl-2',3'-dideoxycytidine, 5-propyl-2',3'-dideoxy-3'-azidocytidine, 5-propene-2',3'-dideoxy-3'-azidocytidine, 5-propyne-2',3'-dideoxy-3'-azidocytidine, and 5-propyne-2',3'-dideoxy-3'-azidocytidine.

33. The method of claim 30, wherein the agent has the structural formula

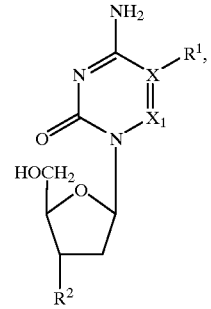

or pharmaceutically acceptable salts thereof.

34. The method of claim 30, wherein in the agent X comprises N and $X^1$ comprises C.

35. The method of claim 30, wherein in the agent X comprises C and $X^1$ comprises N.

36. The method of claim 30, wherein in the agent X comprises N and $X^1$ comprises N.

37. The method of claim 30, further comprising a radiolabel.

38. The method of claim 30, wherein the agent is freeze-dried or lyophilized.

39. The method of claim 30, wherein in the agent the $R^1$ haloalkyl is selected from the group consisting of alkyl substituted by one or more chloro, fluoro, bromo and iodo.

40. The method of claim 39, wherein the agent the $R^1$ fluoralkyl comprises —$CF_3$.

41. The method of claim 30, wherein the disorder is cytosine arabinoside (araC)-resistant leukemia.

42. The method of claim 30, further comprising administering to the subject an anti-leukemia effective amount of an anti-leukemia agent.

43. The method of claim 42, wherein the anti-leukemia agent is administered concurrently with the agent.

44. The method of claim 42, wherein the anti-leukemia agent comprises cytosine arabinoside (araC).

45. The method of claim 30, wherein the disorder comprises arthritis.

46. The method of claim 30, which is a prophylactic method.

47. The method of claim 30, which is a therapeutic method.

48. The method of claim 30, wherein the agent is administered parenterally.

49. The method of claim 30, wherein the agent is administered orally.

50. The method of claim 30, wherein the agent is administered transdermally.

51. The method of claim 30, wherein the agent is administered in an amount of about 0.1 to about 1000 μmol/kg body weight.

52. The method of claim 30, wherein the subject is human.

53. The method of claim 30, wherein the subject is a non-human animal.

54. The method of claim 30, wherein the disorder is a cancer associated with cytidine deaminase or deoxycytidine deaminase overexpression, wherein the agent is administered in an anti-cancer effective amount.

55. The method of claim 54, wherein the cancer is selected from the group consisting of adenocarcinomas, sarcomas, cytomas, melanomas, Wilm's tumors, leukemia and brain prostate, kidney, pancreatic, colon, liver and cervical tumors.

56. The method of claim 55, wherein the brain tumors are selected from the group consisting of gliomas and blastomas.

57. The method of claim 55, wherein the adenocarcinoma is selected from the group consisting of chondrocarcinomas, hepatocarcinomas, basal cell carcinomas and adenocarcinomas of the colon, lung, stomach and breast.

58. The method of claim 55, wherein the cancer is selected from the group consisting of chondrosarcomas, gliomas, astrocytomas, melanomas and sarcomas.

59. The method of claim 56, wherein the blastomas are selected from the group consisting of hepatoblastomas, neuroblastomas and retinoblastomas.

60. The method of claim 55, being a prophylactic method.

61. The method of claim 55, wherein the agent is administered parenterally.

62. The method of claim 55, wherein the agent is administered orally.

63. The method of claim 55, wherein the agent is administered anally.

64. The method of claim 55, wherein the agent is administered transdermally.

65. The method of claim 55, wherein the agent is administered in an amount of about 0.1 to about 1000 μmol/kg body weight.

66. The method of claim 55, wherein the subject is human.

67. The method of claim 55, wherein the subject is a non-human animal.

68. The method of claim 30, wherein the disorder is associated with an increase in number or toxicity of pro-inflammatory cells which over-express cytidine deaminase or deoxycytidine deaminase, wherein the agent is administered in an anti-inflammation effective amount.

69. The method of claim 68, wherein the disorder comprises arthritis.

70. The method of claim 68, being a prophylactic method.

71. The method of claim 68, wherein the agent is administered parenterally.

72. The method of claim 68, wherein the agent is administered orally.

73. The method of claim 68, wherein the agent is administered rectally.

74. The method of claim 68, wherein the agent is administered transdermally.

75. The method of claim 68, wherein the agent is administered in an amount of about 0.1 to about 1000 μmol/kg body weight.

76. The method of claim 68, wherein the subject is human.

77. The method of claim 68, wherein the subject is a non-human animal.

78. The method of claim 30, wherein the disorder is associated with HIV infection, wherein the agent has the chemical formula $C_7N_3H_8O_2R^1R^2XX^1$, wherein X and $X^1$ are each independently C or N but not simultaneously C, $R^1$ is selected from the group consisting of lower alkyl, alkenyl and alkynyl, halogen and haloalkyl, and $R^2$ is selected from the group consisting of H, —$N_3$, —OH and amino or pharmaceutically acceptable salts thereof and is administered in an anti-HIV effective amount.

79. The method of claim 78, wherein $R^1$ is methyl and $R^2$ is —$N_3$.

80. The method of claim 78, wherein the agent is selected from the group consisting of 5-methyl-2',3'-dideoxycytidine, 5-ethyl-2',3'-dideoxy-3'-azidocytidine, 5-propyl-2',3'-dideoxycytidine, 5-propyl-2',3'-dideoxy-3'-azidocytidine, 5-propene-2',3'-dideoxy-3'-azidocytidine, 5-propyne-2',3'-dideoxycytidine, and 5-propyne-2',3'-dideoxy-3'-azidocytidine.

81. The method of claim 78, being a prophylactic method.

82. The method of claim 78, wherein the agent is administered parenterally.

83. The method of claim 78, wherein the agent is administered orally.

84. The method of claim 78, wherein the agent is administered in an amount of about 0.1 to about 1000 μmol/kg body weight.

85. The method of claim 78, wherein the agent is administered anally.

86. The method of claim 78, wherein the agent is administered transdermally.

87. The method of claim 78, wherein the subject is human.

* * * * *